(12) United States Patent
Ponikau et al.

(10) Patent No.: US 7,659,080 B2
(45) Date of Patent: Feb. 9, 2010

(54) DETECTING A BACTERIAL PROCESS IN CHRONIC RHINOSINUSITIS

(75) Inventors: Jens Ponikau, Amherst, NY (US); David Sherris, Buffalo, NY (US); Hirohito Kita, Rochester, MN (US)

(73) Assignees: The Research Foundation of State University of New York, Amherst, NY (US); Mayo Foundation For Medical Education and Research, Rochester, MN (US)

( * ) Notice: Subject to any disclaimer, the term of this patent is extended or adjusted under 35 U.S.C. 154(b) by 0 days.

(21) Appl. No.: 11/897,494

(22) Filed: Aug. 30, 2007

(65) Prior Publication Data

US 2008/0090252 A1   Apr. 17, 2008

Related U.S. Application Data

(60) Provisional application No. 60/841,062, filed on Aug. 30, 2006.

(51) Int. Cl.
*G01N 33/53* (2006.01)
*G01N 33/567* (2006.01)
*G01N 33/00* (2006.01)
*G01N 33/573* (2006.01)
*C12N 9/66* (2006.01)

(52) U.S. Cl. .................. 435/7.1; 435/7.2; 435/7.21; 435/7.24; 435/7.4; 435/218

(58) Field of Classification Search ............ 435/7.1, 435/7.2, 7.21, 7.24, 7.4, 218
See application file for complete search history.

(56) References Cited

U.S. PATENT DOCUMENTS

| | | | |
|---|---|---|---|
| 6,416,955 B1 | 7/2002 | Sherris et al. ............. | 435/29 |
| 6,967,084 B2 | 11/2005 | Small et al. ............... | 435/19 |

2007/0184495 A1   8/2007  Shaari

OTHER PUBLICATIONS

Ogata et al. Auris Nasus Larynx 24: 279-287, 1997.*
Haxel, et al.; Myeloperoxidase in nasal secretion as a cell-activation marker in acute sinusitis; Am. J. Rhinol., Mar.-Apr. 2004, vol. 18, No. 2; pp. 93-98.
Hamaguchi, et al.; ELISA for Determination of Immunoreactive Free Elastase and Elastase in Complex with $\alpha_1$-antitrypsin in Nasal Secretions with Sinusitis; Acta Otolaryngol (Stockh), 1991, vol. 111; pp. 542-549.
Hamaguchi, et al.; Neutrophil Elastase and Its Complex with $\alpha_1$-antitrypsin in Soluble and Insoluble Fractions of Nasal Secretions of Chronic Sinusitis; Acta Otolaryngol (Stockh), 1991, vol. 111; pp. 954-959.
Dunnette, et al.; Microbiologic analyses of nasal polyp tissue; Journal of Allergy and Clinical Immunology, 1986, vol. 78; pp. 102-108.
Belaaouaj; Neutrophil elastase-mediated killing of bacteria: lessons from targeted mutagenesis; Microbes and Infection, 2002, vol. 4; pp. 1259-1264.
Grevers, et al.; Involvement of inferior turbinate mucosa in chronic sinusitis—localization of T-cell subset; Department of Otorhinolaryngology, Head and Neck Surgery, accepted for publication Jul. 6, 2000; Abstract; 10 pages.
Riechelmann, H., et al., "Nasal biomarker profiles in acute and chronic rhinosinusitis", Clinical and Experimental Allergy, Sep. 2005, pp. 1186-1191, vol. 35, issue 9, Blackwell Publishing Ltd.

* cited by examiner

*Primary Examiner*—S. Devi
(74) *Attorney, Agent, or Firm*—Hodgson Russ LLP

(57) ABSTRACT

The present invention provides a method for identifying bacterial induced rhinosinusitis. The method comprises obtaining a nasal or paranasal mucus sample and detecting the presence of neutrophil degranulation in the mucus sample. Degranulation of neutrophils can be determined by morphological analysis of the cells in the mucus or by detection of released (i.e., "free") granule content markers such as neutrophil elastase or myeloperoxidase. Based on an accurate determination of the cause of sinusitis as described herein, an appropriate treatment can be instituted.

6 Claims, 3 Drawing Sheets
(2 of 3 Drawing Sheet(s) Filed in Color)

DETECTING A BACTERIAL PROCESS IN CHRONIC RHINOSINUSITIS

This application claims priority to U.S. provisional application No. 60/841,062, filed on Aug. 30, 2006, the disclosure of which is incorporated herein by reference.

FIELD OF THE INVENTION

The present invention relates generally to the field of sinusitis and more particularly provides a method for identifying bacterial induced rhinosinusitis.

BACKGROUND OF THE INVENTION:

Chronic Rhinosinusitis (CRS, formerly called chronic sinusitis) is an inflammatory disease of the mucosal lining of the sinuses and the nasal cavity. In the US, 32 million adult patients are estimated to have CRS. Two different kinds of white blood cells, eosinophils and neutrophils, mediate the inflammation. While the eosinophils mediate chronic inflammation, neutrophils mediate acute exacerbations of CRS. The eosinophilic inflammation is directed against fungi, neutrophils are recruited as an immune response against bacteria. Identification of bacterial and/or fungal cause of rhinosinusitis would help physicians in differentiating between acute sinusitis, acute exacerbation of CRS and CRS.

Prior studies have not been successful in accurately predicting a bacterial basis of rhinosinusitis. For example, Grevers et al. (Allergy, 55(12); 1155-1162, December 2000) demonstrated the presence of neutrophils in nasal tissue of patients with CRS. However, we have not found this to be a reliable predictor of bacterial sinusitis.

Hamaguchi et al. (1991A, Acta Otolaryngol., (Stockh), 111(3):542-549; 1991B, Acta Otolaryngol., (Stockh), 111 (3):954-959) studied the presence of neutrophils in the mucus of patients with Chronic Sinusitis. All samples were found to be positive for neurtrophile elastase (NE). However, it should be noted that in their analysis, samples were frozen, thawed and then homogenized before analysis for determination of NE. This analysis is therefore flawed in that homogenization would result in breakup of cells and, hence, artifactual release of granule content. Thus, although Hamaguchi et al. refer to measurement of "free" elastase, these authors are not measuring NE released from the neutrophil granules in response to a bacterial sinusitis. Rather, the "free" elastase is a term used in this reference for NE that is not complexed with inhibitors such as $\alpha$1-antitrypsin. This brings into question the reliability of such identification, particularly in the absence of negative controls.

As a result, there is an ongoing need in the field of sinusitis to identify methods for reliable identification of inflammatory causes such that proper treatment regimen can be implemented by health care providers.

SUMMARY OF THE INVENTION

The present invention provides a method for identification of bacterial sinusitis. The method comprises obtaining a nasal or paranasal mucus sample from a patient such that breakup of cells is minimized. The mucus is then analyzed for the presence of neutrophil degranulation. Degranulation of neutrophils can be determined by morphological analysis of the cells in the mucus or by detection of released (i.e., "free") granule content markers in the mucus. In one embodiment, the neutrophil granule conent marker is neutrophil elastase (NE). In another embodiment, the neutrophil granule conent marker is myeloperoxidase (MPO). The presence of free nuetrophil granule content marker or indication of degranulation by morphological analysis is indicative of bacterial sinusitis. Optionally, as a futher step, degranulation of eosinophils can also be evaluated to determine if rhinosinusitis is caused by both bacteria and fungi.

Based on an accurate determination of the cause of sinusitis as described herein, an appropriate treatment can be instituted.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE INVENTION

Figure 1:
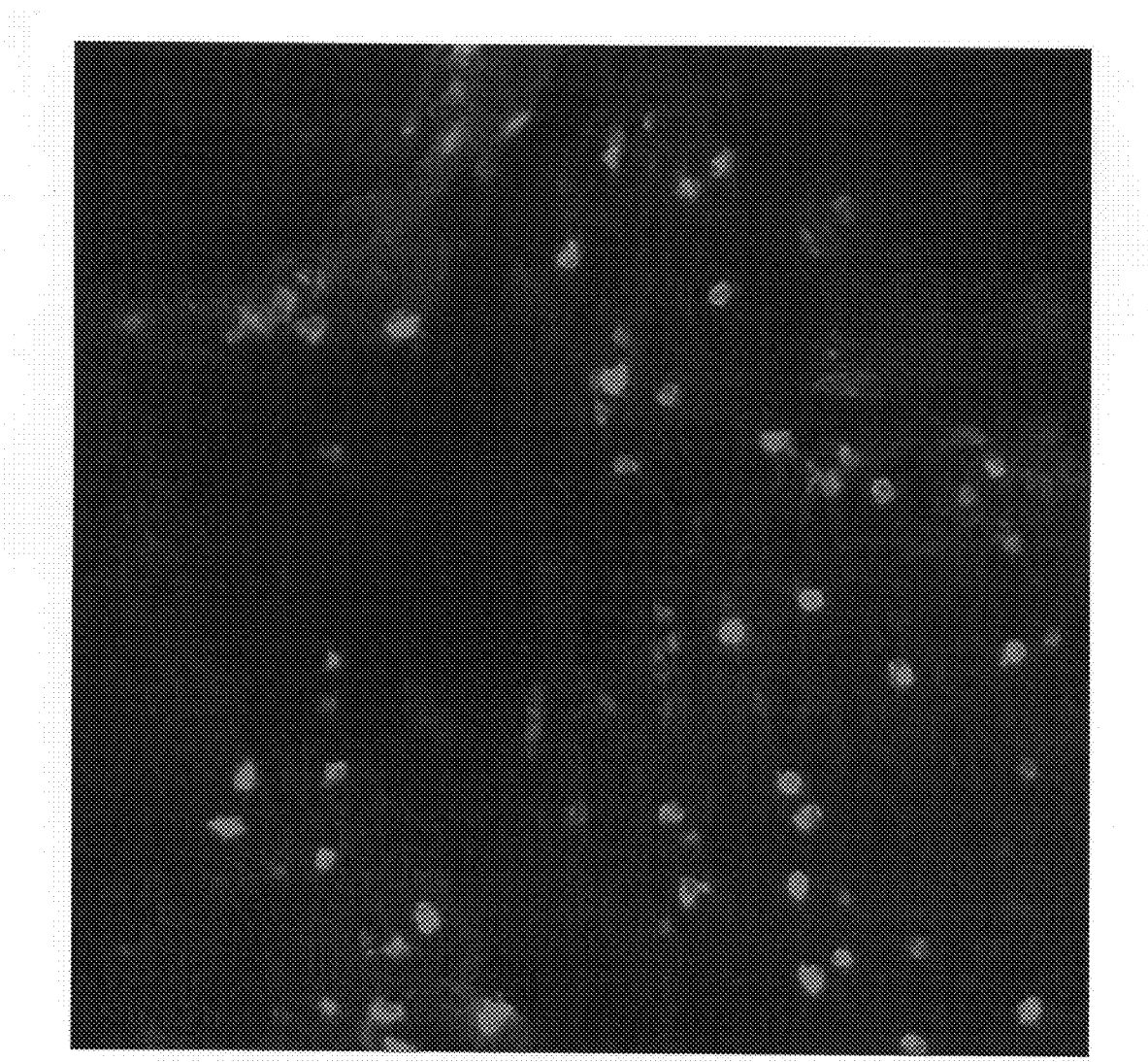
FIG. 1 shows nasal tissue from CRS patient stained with an antibody (rabbit antihuman elastase (IgG fraction, Cortex Biochem, San Leandro, Calif.)) to neutrophil elastase (NE). NE is within the intact cell.

The present invention provides a method for determining if a sinusitis condition is caused by bacteria. The determination is made by identifying neutrophil degranulation in the nasal or paranasal mucus. The invention is based on the unexpected observation that bacterial rhinosinusitis can be reliably diagnosed by detecting the presence of neutrophil degranulation in the nasal or paranasal mucus. Further, it was observed that during bacterial rhinosinusitis, neutrophils in blood as well as within tissue appear to contain intact granules and we have also observed that neutrophils rarely release their granules within the nasal tissue. However, during bacterial rhinosinusitis, neutrophils are released into the mucus wherein degranulation with release of the granule contents takes place. It is important to note that the mere presence of neutrophils in the mucus is not indicative of a bacterial sinusitis. Rather, it is the degranulation of neutrophils in the mucus that is indicative of bacterial sinusitis. As a result, it is important to process the mucus samples so as to avoid or minimize breakup of any leukocytes (including neutrophils) present and so that released (also termed herein as "free") granule contents of neutrophils can be identified without interference from the granule contents within intact granules in the neutrophils. By "no significant breakup" of cells is meant that intact cells (leukocytes) can be clearly identified in the mucus if a morphological analysis is performed.

By "released" or "free" neutrophil granule content is meant the granule content that is released into the environment (such as mucus) by neutrophils in response to challenge from bacteria. To selectively measure free granule content, there should be no or minimal interference from the intact granule contents. By "selective detection of free neutrophil granule content" is meant that the mucus sample is processed using methods which are not expected to cause breakup of cells. Therefore, processes known to breakup cells such as homogenization or sonication or ultrasonication should be avoided. However, vortexing (or other similar steps) of samples to get a homogenous distribution of components without breakup of cells can be carried out.

A mucus sample can be collected from an individual and analyzed to determine whether or not the patient's mucus contains degranulated or degranulating neutrophils. Mucus collection methds are generally described in U.S. Pat. No. 6,416,955 to Sherris, which method desriptions are incorporated herein by reference. Mucus can be collected from any mucosal tissue by using a standard collection solution to flush the mucus-containing cavity. Proper mucus collection techniques are well known in the art and maximize recovery of a mucus-containing collection solution by allowing sufficient penetration of the appropriate anatomic cavities and by minimizing collection solution absorption by the individual. Vasoconstrictor agents can be used to maximize mucus collection and mucolytic agents can be used to dissolve obstructive mucus such that collection solution penetration is enhanced.

Before collecting a mucus sample, an individual can be treated with a vasoconstrictor agent and/or a mucolytic agent such that sufficient vasoconstriction and/or mucolytic action is induced in the appropriate region. Suitable vasoconstrictor agents can include, without limitation, phenylephrine hydrochloride (NEO-SYNEPHRINE™; Sanofi Pharmaceuticals), cocaine, and epinephrine. A mucolytic agent is any agent that liquefies mucus such that it can be recovered from the patient. Suitable mucolytic agents can include, without limitation, N-acetyl-L-cysteine (MUCOSIL™; Dey Laboratories) and recombinant human DNase (PULMOZYME™; Genentech, Inc.). Any administered vasoconstrictor agent or mucolytic agent should be allowed to take effect by waiting a sufficient period of time after administration such as about two to five minutes.

The following methods and materials can be used to collect a nasal-paranasal mucus sample. First, an individual is prepared to receive a collection solution in at least one nostril or nasal-paranasal cavity by directing the individual to inhale and to lower the chin, or in some other way constrict the access of fluids out of the mouth and down the esophagus. In a vertically sitting or standing individual, these maneuvers tend to minimize the loss or ingestion of the collection solution. Other maneuvers are also possible provided this goal is achieved. Second, an injection and collection system is configured. In general, the configuration is such that a collection solution can be administered to an individual's nostril and then efficiently collected in a container. The injection system can be, without limitation, a syringe with a curved blunt needle or tube assembly. The container can be any type of container that holds liquid. In addition, the container can be, without limitation, a storage container that is suitable for use as a transporter or sealable apparatus such that the collected sample can be handled or shipped. These containers also can contain an agent such as a preservative or antibacterial agent depending upon the desired use of the mucus sample. Third, a collection solution is administered into an individual's nostril and collected. Before administration, the individual can be instructed to expel the collection solution upon sensing the fluid in the nasal-paranasal anatomy. Alternatively, the individual can be instructed to expel the collection solution simultaneously with the administration. During administration, the collection solution can be forcibly injected into at least one nostril or side of the nasal-paranasal anatomy. The volume of the collection solution can vary according to the individual and the state of the mucositis. For example, fluid volumes can be, without limitation, between about 0.1 mL to about 100 mL or more, and specifically between about 0.1 mL and about 25 mL. The collection solution can be, without limitation, a saline solution, water, and any other suitable solution appropriate for contacting mucosal tissue. In addition, the collection solution can contain other agents that may be useful for the collection of mucus such as a mucolytic agent.

One goal of a collection solution is to dislodge and remove mucus within mucus-containing cavities. In addition to a collection solution acting as a natural flushing agent, the penetrating effect of a mucolytic agent within a collection solution can help liquefy thick obstructive mucus. Further, the combination of the force of administration with the near simultaneous pressurized expulsion by an individual can help dislodge and collect mucus. Typically, a collection solution can be administered during a period of less than about five seconds per side. In addition, a collection solution can be administered during a period of less than about three seconds. Alternatively, the time period of collection solution administration can be extend beyond five seconds depending on specific factors such as the degree of inflammation, the presence of obstructions, and the size of the individual. In addition, an administration greater than five second can be used when very small volumes or streams of collection solution are desired.

Other collection procedures also can be used to collect mucus samples, particularly if an individual is unable to comply or cope with a liquid collection procedure. Such additional procedures are well known in the art and include, without limitation, the surgical removal of mucus, a swab or mechanical mucus extraction procedure, and pressure or vacuum systems that extract mucus.

Figure 3:
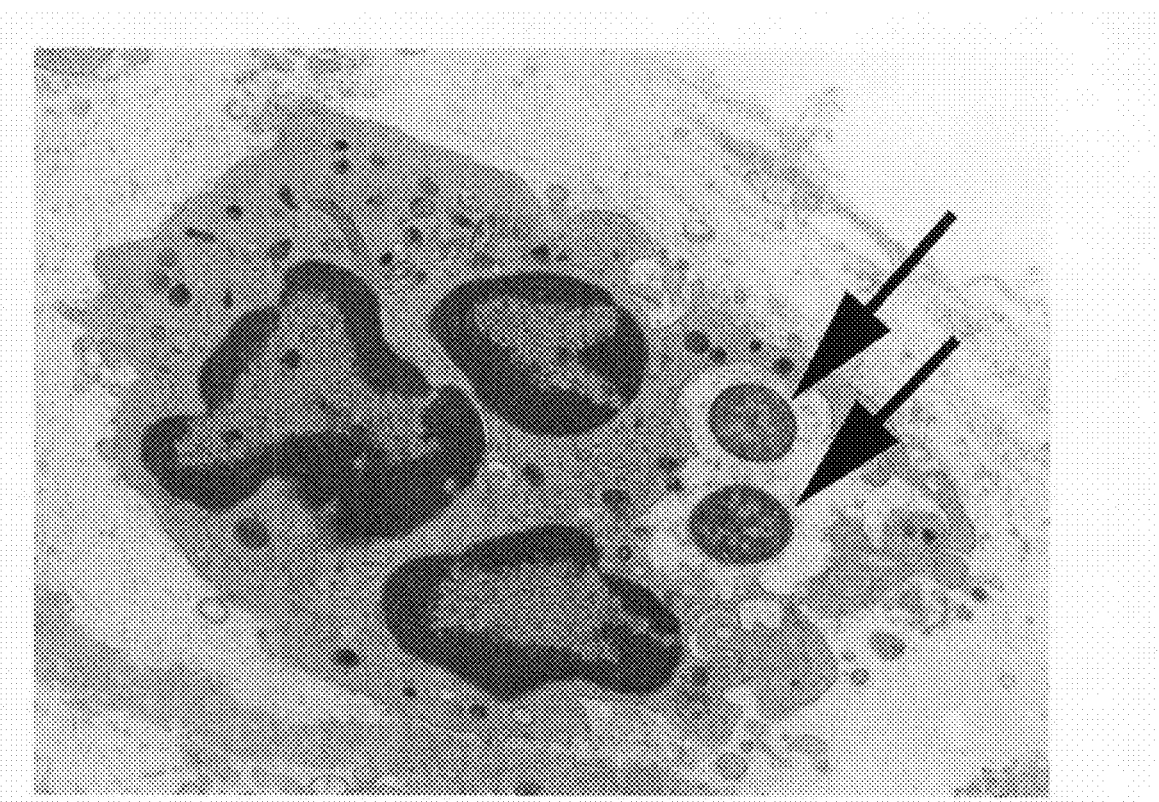
FIG. 3 is a Transmission electron micrograph of the mucus showing a neutrophil which has phagocytosed bacteria (black arrow). This demonstrates that neutrophils are targeting bacteria in the sinus lumen of CRS patients FIG. 4 Graph shows IL-8 measurement of human immune cells (peripheral blood mononuclear cells, PBMCs) after stimulation (incubation) with different bacterial culture extract containing bacterial antigens.

Once collected, the mucus sample can be analyzed to determine whether or not the patient's mucus contains degranulated neutrophils. Neutrophil degranulation can be identified by visualization of neutrophil morphology (such as by high power light microscopy or electron microscopy) or by detection of released granule contents in the mucus. For morphological analysis, identification of neutrophils containing bacteria (as shown in FIG. 3) would be indicative of a degranulation condition of the neutrophils.

The mucus samples can be processed or stored frozen and processed at a later time. The collected mucus can be vortexed to mix the mucus. Mucus, particularly from an individual with rhinosinusitis generally contains cellular material in a liquid medium. Generally, vortexing (such as at low or medium speed) using a standard lab vortex does not cause any significant break up of the cells. The cells can be separated from the liquid medium. For example, the mucus can be centrifuged to separate out the cellular component (such as leukocytes) from the non-cellular medium (i.e., the supernatant or the liquid medium). The supernatant can be used for detection of one or more neutrophil granule content markers.

Released granule contents can be detected by biochemical or immunological assays. The presence of an amount of neutrophil granule content that is significantly higher than a normal control indicates that the patient has a neutrophil degranulating condition and therefore a bacterial induced rhinosinusitis. Such an amount is expected to cause damage to the epithelial cells within the body anatomy from which the mucus was collected and can be termed as a "tissue-damaging amount". As discussed above, for the purpose of this invention, granule content is considered to be in free form once released from a neutrophil granule. The term "neutrophil granule content" as used herein refers to any molecule contained within a neutrophil which would be distinct over the granule content of other cells in the mucus such as eosinophils. Thus, neutrophil granule content can include neutrophil elastase (NE) or myeloperoxidase (MPO).

In general, the amount of released neutrophil granule content within the nasal/paranasal mucus of acute rhinosinusitis (including acute exacerbation of CRS) patients is significantly higher than a normal control, while the amount within the nasal/paranasal mucus of allergic rhinitis patients or chronic rhinosinusitis is not. While the mucus of allergic rhinitis patients or chronic rhinosinusitis patients may contain neutrophils, the contents of these neutrophils would not be released and therefore not free. Thus, any method that can detect free neutrophil granule content can be used. Such methods include, without limitation, affinity binding assays that use a binding agent (e.g., antibody, receptor, ligand, etc.) to detect free neutrophil granule content marker. Such binding agents include, without limitation, antibodies having specificity for NE or MPO. Immunological assays are routine in the art and generally involve detection via a specific antibody to the analyte. The antibody may be a monoclonal antibody, a polyclonal antibody, a scFV and any other antigen binding fragment of a natural antibody, a chimeric antibody or a synthetic antibody. A second antibody may also be used for easy detection. The primary or the secondary antibody is detectably labeled by using a fluorescent marker, a color developing agent (such as biotin) or particulate markers (such as gold). Additionally, mobilization via binding to a solid support can also be carried out. For example, an anti-NE antibody can be immobilized to a solid support, a mucus sample can be applied to the immobilized antibody such that any free NE is captured, and a second labeled anti-NE antibody can be used to detect any captured NE. In these types of immunological assays, a simple color reaction can be used to identify mucus samples containing free neutrophil granule content.

To analyze the cell-free supernatant obtained after centrifugation of mucus samples, standard immunological assays can be used. For example, for detection of NE or MPO, it is convenient to use ELISA assays using commercially available reagents.

Upon positive identification of bacterial sinusitis, an appropriate regimen of antibiotics can be implemented for treatment. In one embodiment, the mucus can also be tested for the presence of degranulated eosinophils as described in U.S. Pat. No. 6,416,955. Thus, in addition to detectin of neutrophil granule content marker, one or eosiniophil granule content markers (such as major basis protein or MBP) can also be detected. By a comibation of these two methods, the following determinations and treatment regimens can be instituted.

TABLE 1

| Condition | Degranulated Eosinophils | Degranulated Neutrophils | Treatment |
| --- | --- | --- | --- |
| Chronic rhinosinusitis | + | − | Steroids, Antifungals |
| Acute exacerbation of chronic rhinosinusitis | + | + | Steroids Antifungals Antibiotics |
| Recurrent Acute Sinusitis | − | + | Antibiotics |
| Acute Sinusitis | − | + | Antibiotics |

In another embodiment, the degranulation of neutrophils can be used to determine if a particular antibiotic is effectively treating the bacterial sinusitis. Depending upon the results, the treatment can be continued or altered.

EXAMPLE 1

Figure 2:
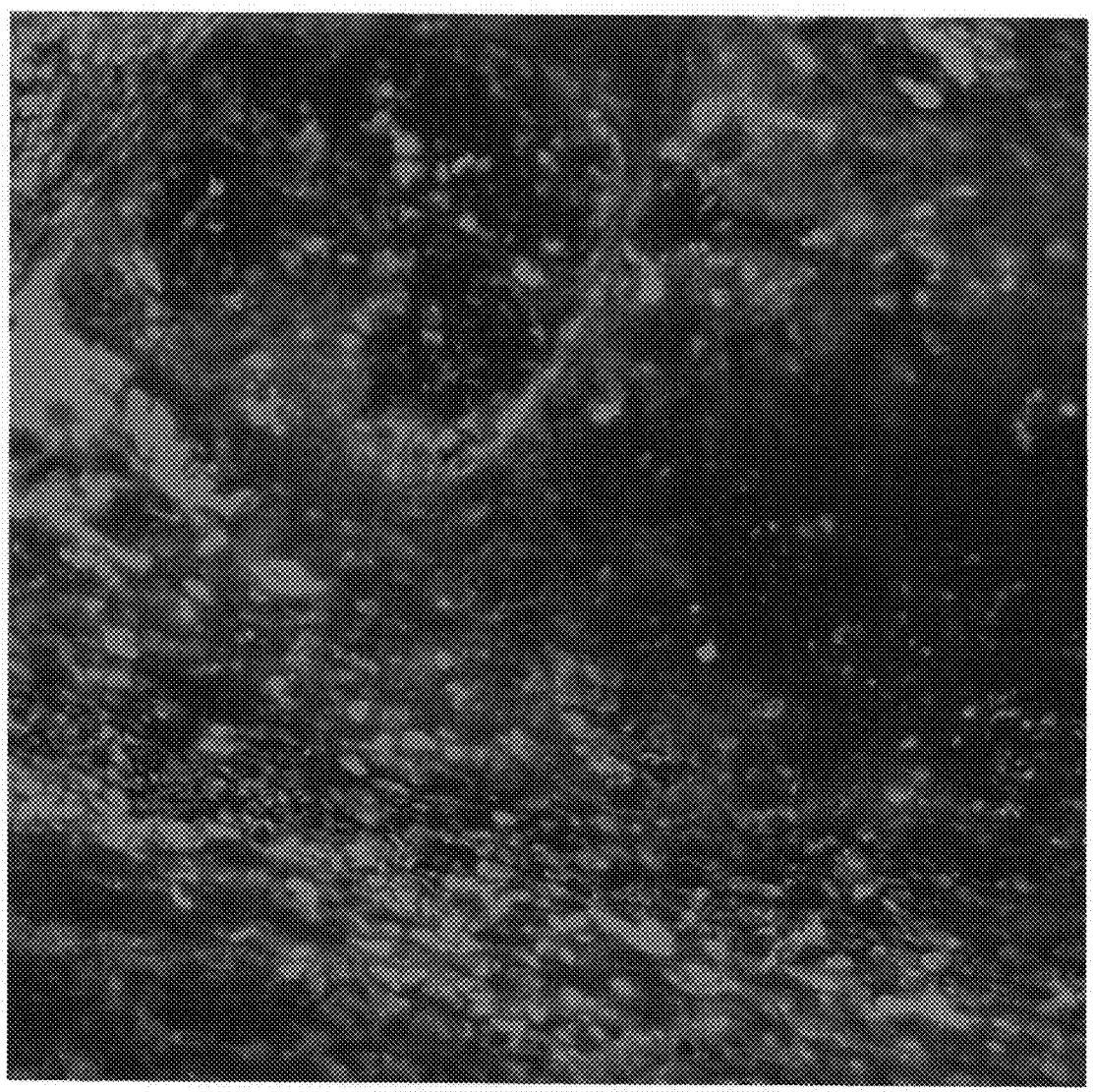
FIG. 2 shows mucus stained with an antibody to neutrophil elastase (NE). The neutrophils are degranulating and release NE into the mucus (extra-cellular staining) indicating a bacterial sinusitis.

In this example, detection of free neutrophil granule content marker, NE, was carried out in a nasal tissue sample and a mucus sample. Immunoflorescent localization was carried out using a rabbit anti-human antibody to NE. A second fluorescein labeled antibody was used for visualization. The results are shown in FIGS. 1 and 2. Staining inside the cells can be seen in the nasal tissue sample indicating that the neutrophil granules are intact and the contents have not been released into the environment. However, in FIG. 2, the staining is extracellular indicating degranulation and release of the neutrophil granule contents into the mucus.

EXAMPLE 2

Figure 4:
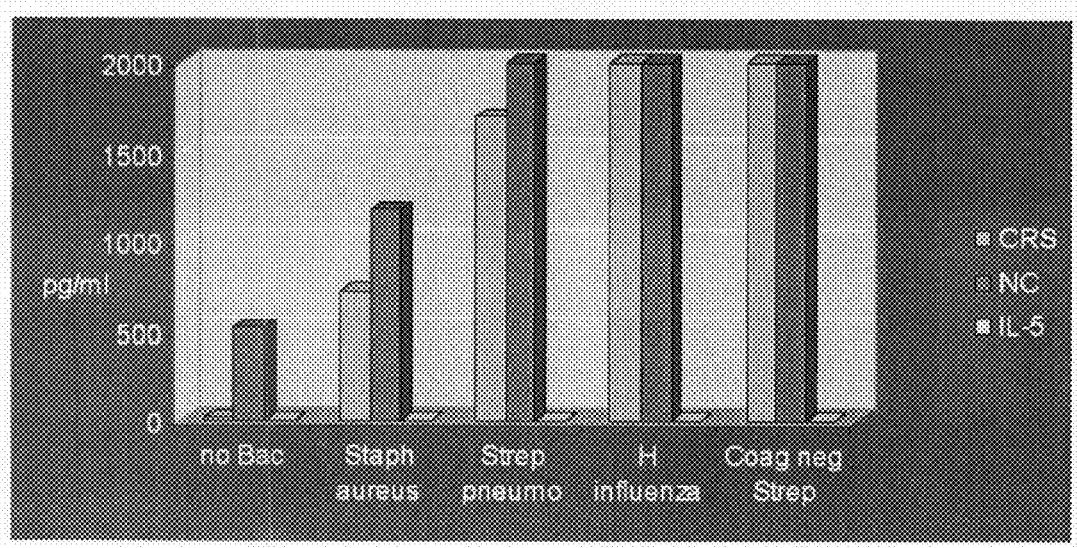

This example demonstrates that neutrophil response is mounted when the nasal epithelium encounters bacteria. IL-8 was measured in human immune cells (peripheral blood mononuclear cells, PBMCs) after stimulation (incubation) with different bacterial culture extract containing bacterial antigens. The key cytokine for the recruitment of neutrophils is IL-8, the key cytokine for the recruitment of eosinophils is IL-5. The results are shown in FIG. 4. After incubation, no IL-5 was produced by patients and healthy controls, but large amounts of IL-8 were produced. This demonstrates that a neutrophilic, but not an eosinophilic, inflammation is produced by the human immune system when it recognizes a bacterium or bacterial products. Detecting substances which are important in the recruitment of neutrophils into the tissue, or neutrophils or its products, demonstrates that bacteria or its byproducts have induced the inflammation.

EXAMPLE 3

This example describes the processing of mucus samples from patients and analysis of the samples for the presence of free form of NE as a marker for degranulation of neutrophil. Nasal secretions were obtained under endoscopic guidance by using a sterile sinus secretion collector (Xomed Surgical Products, Jacksonville, Fla.). Each secretion specimen was extracted by adding twice the volume of 0.9% NaCl, vortexing 3 times for 10 seconds, and centrifugation at 40000 g for 20 minutes. The supernatants were stored at −20° C.

As a marker of neutrophilic degranulation, the concentration of elastase in the supernatants was quantitated by the ENZCHEK® Elastase Assay Kit (Molecular Probes, Eugene, Oreg.), following the procedure recommended by the manufacturer. Molecular Probes ENZCHEK® Elastase Assay Kit (E-12056) contains soluble bovine neck ligament elastin (DQ™elastin) that has been labeled with BODIPY® FL dye so that the conjugate's fluorescence is quenched. The non-fluorescent substrate is digested by elastase to yield highly fluorescence fragments that can be measured by a fluorescence microplate reader. Digestion products from the DQ™ elastin substrate have absorption maxima at 515 nm.

The kit reagents were brought to room temperature before opening vials. The stock solution of DQ™ elastin substrate was prepared by adding 1 mL of deionized water to the vial. A working solution of 100 ug/mL was obtained by diluting the stock tenfold in Reaction Buffer(1M Tris-HCl, pH 8.0). A 50 uL volume was be used for each 200 uL reaction tube. A standard curve was prepared by reconstituting a vial of porcine pancreatic elastase with 0.5 mL dH2O. Concentration of this solution was 100 U/mL. The stock solution was diluted 1:200 in assay Reaction Buffer for a final concentration of 0.5 U/mL (3700 ng protein/mL). Further dilutions of this solution were made so that a seven point standard curve was established (0.5, 0.25, 0.15, 0.1, 0.05, 0.025, 0.01 U/mL). All samples were diluted 1:4 in Reaction Buffer. To a COSTAR® 96 well clear bottom, black plate(#3603), 50 uL of Reaction Buffer was added to each well. Next, standards and samples were added, 100 uL per well. Next, 50 uL per well of DQ™ Elastin was added. Samples were incubated at room temperature for one hour. Florescence was monitored every 10 minutes by reading plate on a fluorescence plate reader set for 485 nm excitation and 530 nm emission. The sensitivity of assay was 0.07 microgram/ml.

Results for 22 samples as well as one healthy control are shown in Table 2. The data shows that 21/22 had elevated eosinophil MBP in the nasal/paranasal secretions, which confirms degranulating eosinophils and the diagnosis of chronic rhinosinusitis. Only 2 samples (samples 7 and 8) had elevated NE present, confirming an additional bacterial process. Thus, only the 2 samples with elevated NE are appropriate for treatment with an antibiotic in addition to an anti-fungal agent. Administration of antibiotics to the remaining patients, on the other hand, would not alleviate the symptoms and the appropriate treatment for those would be anti-fungal agents only.

TABLE 2

| Sample | Indication | ug/ml Elastase | U/ml Elastase | µg/ml MBP |
|---|---|---|---|---|
| 1 | CRS | <.07 | <.01 | 0.22 |
| 2 | CRS | <.07 | <.01 | 54.50 |
| 3 | CRS | <.07 | <.01 | 43.90 |
| 4 | CRS | <.07 | <.01 | 4.31 |
| 5 | CRS | <.07 | <.01 | 1.22 |
| 6 | CRS | <.07 | <.01 | 1.98 |
| 7 | CRS | 6.87 | 0.928 | 2.73 |
| 8 | CRS | 10.1 | 1.36 | 3.65 |
| 9 | CRS | <.07 | <.01 | 4.62 |
| 10 | CRS | <.07 | <.01 | 4.91 |
| 11 | CRS | <.07 | <.01 | 4.64 |
| 12 | CRS | <.07 | <.01 | 5.67 |
| 13 | CRS | <.07 | <.01 | 4.07 |
| 14 | CRS | <.07 | <.01 | 11.79 |
| 15 | CRS | <.07 | <.01 | 0.67 |
| 16 | CRS | <.07 | <.01 | 8.91 |
| 17 | CRS | <.07 | <.01 | 8.77 |
| 18 | CRS | <.07 | <.01 | 8.99 |
| 19 | CRS | <.07 | <.01 | 12.20 |
| 20 | CRS | <.07 | <.01 | 10.85 |
| 21 | CRS | <.07 | <.01 | 5.92 |
| 22 | CRS | <.07 | <.01 | 5.40 |
| 23 | Normal | <.07 | <.01 | 0.25 |

EXAMPLE 4

This example describes the detection of another neutrophil granule content marker, myeloperoxidase (MPO) in the free form in the mucus of patients. The samples used for this assay are the first 10 samples from Example 1 and the normal control.

MPO was measured using a kit from Hycult biotechnology #HK324. The kit is intended for the quantitative measurement of natural human MPO with a minimum detection level of 0.4 ng/mL. Microtiter wells are precoated with antibody to MPO. Samples were diluted 1:10 in assay diluent (Tris buffered saline with protein). Standard MPO was reconstituted with 0.5 mL of distilled water. Final concentration of this was 310 ng/mL. This stock standard was diluted to a concentration of 100 ng/mL with assay diluent. A serial dilution of 2:5 parts was made for the rest of the standard (40, 14, 6.4, 2.6, 1, and 0.4 ng/mL. The samples and standards were added to the coated wells at 100 uL per well and incubated for one hour at room temperature. The plate was washed 4 times with washing buffer (Tris buffered saline with Tween). Then the biotinylated antibody was added to the wells and incubated for another hour and washed again. Strepavidin-HRP was reconstituted and further diluted 1:24 parts. 100 uL per well was added and the plate was incubated for one hour. After washing 4 times, 100 uL/well of TMB substrate was added. Color development was stopped with 2N $H_2SO_4$ (100 uL/well). Absorbance was read at 450 nm.

The results indicate that 8 of the 10 samples were positive for MPO compared to the normal control. This indicates that MPO can also be used as a marker of neutrophil degranulation.

Although this invention has been described through various embodiments and illustrations, routine modifications will be apparent to those skilled in the art, which modifications are intended to be within the scope of the invention and the claims.

The invention claimed is:

1. A method of detecting bacterial sinusitis in an individual comprising the steps of:
    (a) collecting nasal or paranasal mucus sample from the individual;
    (b) processing the mucus sample by a process which is not expected to cause breakup of neutrophils and
    (c) selectively detecting the presence of the free neutrophil granule content marker, neutrophil elastase, released by the neutrophils in the mucus sample;
    wherein the presence of the free neutrophil elastase released by the neutrophils in the mucus sample compared to a mucus sample from a healthy normal control is indicative of the bacterial sinusitis in the individual.

2. The method of claim 1, wherein the collected mucus sample is centrifuged to obtain a supernatant and the free neutrophil elastase is detected in the supernatant.

3. The method of claim 2, wherein the mucus sample is processed without homogenization.

4. The method of claim 1, wherein the neutrophil elastase is detected using an antibody or an antigen binding fragment thereof specific for the neutrophil elastase.

5. The method of claim 1 further comprising the step of detecting selectively the presence of eosinophil degranulation in the mucus sample.

6. The method of claim 5, wherein the eosinophil degranulation is detected by identifying the presence of free major basic protein in the mucus sample.

* * * * *

UNITED STATES PATENT AND TRADEMARK OFFICE
CERTIFICATE OF CORRECTION

PATENT NO.        : 7,659,080 B2
APPLICATION NO.   : 11/897494
DATED             : February 9, 2010
INVENTOR(S)       : Ponikau et al.

Page 1 of 1

It is certified that error appears in the above-identified patent and that said Letters Patent is hereby corrected as shown below:

Column 1, line 7 should read:

--STATEMENT AS TO FEDERALLY SPONSORED RESEARCH

This invention was made with government support under grant AI049235 awarded by the National Institutes of Health. The government has certain rights in the invention.--

Signed and Sealed this
Thirteenth Day of November, 2012

David J. Kappos
*Director of the United States Patent and Trademark Office*